United States Patent
Hayes

[11] Patent Number: 6,137,109
[45] Date of Patent: Oct. 24, 2000

[54] AUTONOMOUS TANGENTIAL MOTION CONTROL IN A MULTI-DETECTOR GAMMA CAMERA

[75] Inventor: John M. Hayes, Macedonia, Ohio

[73] Assignee: Picker International, Inc., Highland Heights, Ohio

[21] Appl. No.: 09/075,601

[22] Filed: May 11, 1998

Related U.S. Application Data

[60] Provisional application No. 60/048,113, May 30, 1997.

[51] Int. Cl.[7] .................................................. G01T 1/166
[52] U.S. Cl. ....................................................... 250/363.05
[58] Field of Search ........................ 250/363.05, 363.08, 250/362, 363.02

[56] References Cited

U.S. PATENT DOCUMENTS

| | | | |
|---|---|---|---|
| 3,777,145 | 12/1973 | Brunnett et al. | 250/363.02 |
| 5,206,512 | 4/1993 | Iwao | 250/363.05 |
| 5,349,190 | 9/1994 | Hines et al. | 250/363.05 |
| 5,691,538 | 11/1997 | Ohike et al. | 250/363.05 |

FOREIGN PATENT DOCUMENTS

| | | |
|---|---|---|
| 2 697 918 | 5/1994 | France . |
| WO 92/07512 | 5/1992 | WIPO . |

*Primary Examiner*—Constantine Hannaher
*Assistant Examiner*—Albert Gagliardi
*Attorney, Agent, or Firm*—Timothy B. Gurin; John J. Fry; Eugene E. Clair

[57] ABSTRACT

The configuration of a multi-head gamma camera requires coordination between tangential and radial motions so that the detectors maintain a desired orientation, either corner to corner or overlapping. Based on the radial and angular positions of the detectors, desired tangential positions are determined. The desired tangential positions are compared with the actual tangential positions, to generate position error signals. Tangential motion is initiated to reduce the position errors. If the required tangential motion exceeds the capability of the tangential drive or cannot be achieved, the radial motion is slowed or stopped.

16 Claims, 8 Drawing Sheets

Initially, tangents = 0,
radii = 19cm

1) Radius 1 move -4cm
2) Tangent 1 move tan 30° * 4cm = +2.3cm
3) Tangent 3 move 4.0cm/sin60° = +4.62cm

------------------

4) Radius 2 move -4cm
5) Tangent 2 move +2.3cm
6) Tangent 1 move +4.62cm

------------------

7) Radius 3 move -4cm
8) Tangent 3 move +2.3cm
9) Tangent 2 move +4.62cm

Therefore, detectors, 1,2 & 3 must all be moved tangentially by 6.92cm to permit the desired radial motion.

6,137,109

AUTONOMOUS TANGENTIAL MOTION CONTROL IN A MULTI-DETECTOR GAMMA CAMERA

BACKGROUND OF THE INVENTION

The present application claims benefit of provisional application Ser. No. 60/048,113 filed May 30, 1997.

The present invention relates to the nuclear medicine art. It finds particular application in conjunction with multiple detector single photon emission computed tomography (SPECT) and positron coincidence detection (PCD) systems and will be described with particular reference thereto.

Early nuclear or Anger cameras had a single radiation detector head which was positioned stationarily over a region of interest of the subject. The subject was injected with a radio-pharmaceutical. Some of the radiation given off by the radionuclide was received by the gamma camera detector head which converted the radiation event into light.

More specifically, the detector head included a scintillator which converted each received radiation event into a scintillation or flash of light. An array of photomultiplier tubes positioned in the back of the scintillator and associated circuitry determined an (x,y) coordinate location and an energy (z) value for each scintillation event. A collimator including a grid-like array of lead vanes limited the path or trajectory of radiation events which could strike the scintillator. The collimator must be positioned as close to the patient as possible to acquired image data required to generate high resolution images. In this matter, an image of the radiation events in the examined region of the subject was developed.

In SPECT imaging, one or more detectors are rotated around the subject or indexed to a multiplicity of angularly offset positions around the subject to collect data which is the mathematical equivalent of a CT scanner data set. In PCD imaging, two or more detectors may be rotated about the patient or scanned longitudinally in relation to the patient.

The detectors may advantageously be placed in various angular relationships to each other. In whole body imaging, two detector heads are positioned on opposite sides of the patient. For other studies, particularly cardiac studies, it is advantageous to position the detector heads orthogonally to each other. Still other systems have three heads placed at 120 degree intervals about the subject. In each case, the detector face is placed as close as possible to the patient during imaging.

Each of the foregoing systems has various advantages and disadvantages. Systems having two opposed detector heads are particularly useful for whole-body imaging. Wide field of view detectors, which permit scanning of the entire width of the body, are preferably used in this application. Systems having two orthogonal detectors are commonly used for cardiac imaging. Because a wide field of view is not required in cardiac applications, smaller detectors are preferably used to allow the detectors to be placed as close as possible to the patient. Three detector head systems are often used in connection with high resolution brain and cardiac imaging. Although wide field of view detectors are desirable for body imaging, their physical size again limits their performance in head imaging. These tradeoffs limit the versatility of traditional gamma camera systems.

The present invention addresses the above referenced tradeoffs, and others.

SUMMARY

According to a first aspect of the present invention, an imaging method utilizing a gamma camera having first and second detectors disposed about an examination region is provided. The method includes placing the detectors in a desired position with respect to the examination, utilizing the detectors to detect radiation, and generating an image indicative of the detected radiation. The step of placing includes determining an actual position of the first detector and moving the second detector based on the actual position of the first detector.

According to a more limited aspect of the present invention, the first detector is movable in a radial direction with respect to the examination region and the second detector is movable in a tangential direction with respect to the examination region. The step of placing includes determining an actual radial position of the first detector and moving the second detector in a tangential direction based on the actual radial position of the first detector.

According to another limited aspect of the present invention, the step of placing includes determining a desired motion for the second detector based on the actual position of the first detector, comparing the desired motion to a limit, and limiting a motion of the first detector if the desired motion exceeds the limit.

According to a yet more limited aspect, the method includes determining a desired tangential motion for the second detector based on the actual radial position of the first detector. According to a still more limited aspect, the gamma camera includes a third detector. The method includes determining a desired tangential motion for the second detector based on the actual radial positions of the first and third detectors. According to another still more limited aspect, the step of determining a desired motion includes determining a desired velocity, the limit includes a limit velocity, and the step of comparing includes comparing the desired velocity to the limit velocity. According to yet more limited aspect, the step of determining a velocity includes determining difference between the actual position of he second detector and the desired position of the second detector and determining a velocity required for the second detector to reach the actual position with a first time period.

According to another more limited aspect of the present invention, the step of determining a desired motion includes determining a desired position, the limit includes a limit position, and the step of comparing includes comparing the desired position to the limit position.

According to still another more limited aspect of the present invention, the step of limiting a motion includes limiting velocity of the first detector.

According to another limited aspect of the present invention, the gamma camera includes a third detector. The step of placing includes determining an actual position of the first, second, and third detectors, moving the second detector based on the actual position of the first and third detectors, and moving the third detector based on the actual position of the first and second detectors.

According to a more limited aspect of the invention, the first, second, and third detectors are each movable radially with respect to the examination region and tangentially with respect to the examination region. The step of placing includes determining an actual radial position of the first, second, and third detectors, moving the first detector in a tangential direction based on the actual radial positions of the second and third detectors, moving the second detector in a tangential direction based on the actual radial position of the first and third detectors, and moving the third detector in a tangential direction based on the actual radial positions of the fist and second detectors. The detectors may be disposed at equal angular increments about the examination region.

According to another aspect, the present invention provides a method of imaging using a gamma camera having first and second detectors disposed about an examination region. The method includes placing the detectors in a desired position with respect to the examination region, utilizing the detectors to detect radiation, and generating an image indicative of the detected radiation. The step of placing includes determining a position of the first detector, determining a desired motion for the second detector based on the position of the first detector, comparing the desired motion to a limit, and limiting a motion of the first detector if the desired motion exceeds the limit.

According to another aspect of the present invention, a gamma camera includes first, second, and third detectors disposed about an examination region. A method of positioning the detectors with respect to the examination region includes determining a radial position of the second and third detectors, utilizing the radial positions of the second and third detectors to determining a desired tangential velocity for the first detector, and comparing the desired tangential velocity to a limit velocity. If the desired tangential velocity is greater than the limit velocity, the radial velocity of at least one of the second and third detectors is limited.

Still other aspects of the present invention will be appreciated by those skilled in the art upon reading and understanding the appended detailed description.

DRAWINGS

DESCRIPTION

The present invention is preferably implemented in conjunction with a multiple head gamma camera in which one or more of the detectors heads ar movable both tangentially and radially in relation to the examination region. The detector heads may also be movable to various angular relationships relative to each other. A suitable gamma camera system is disclosed in U.S. application Ser. No. 08/757/874, entitled Variable Angle Multiple Detector Nuclear Medicine Gantry, assigned to Picker International, Inc.

Figure 1:
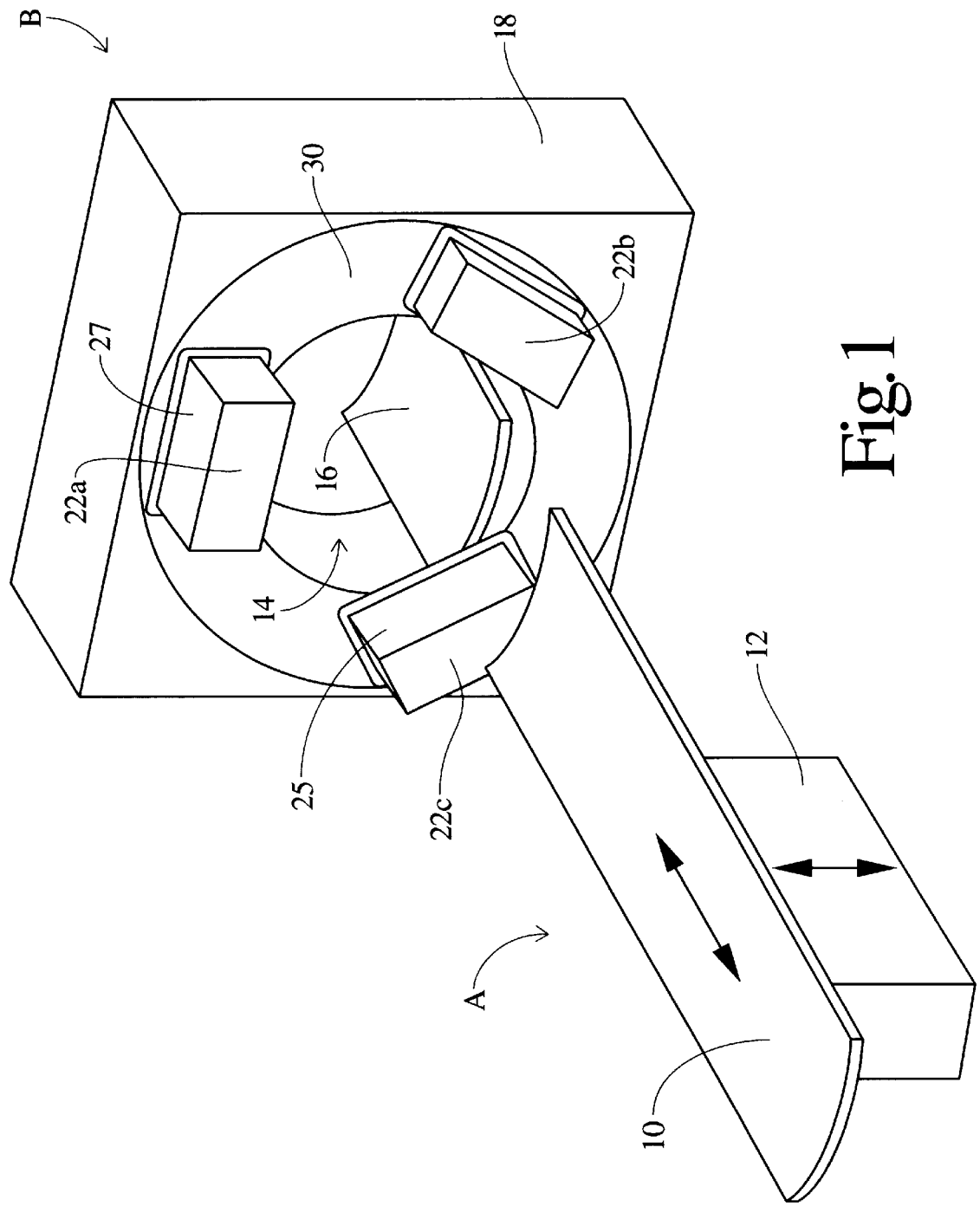
FIG. 1 depicts a front perspective view of a gamma camera.

With reference to FIG. 1, a patient is supported on a patient support A. The patient support includes a thin, relatively radiation transmissive support surface 10 which is mounted cantilevered from a base 12. The base includes motors for raising and lowering the patient support surface and for extending and retracting the support surface relative to a nuclear camera gantry B.

The gantry B includes stationary 18 and rotating 30 gantry portions. Detectors 22a, 22b, 22c are mounted to the rotating gantry portion 30 and define an aperture into which the anatomy of a patient may be inserted. Each detector 22 has a body 27 and a face 25. Each detector is characterized by a width w. As the gantry rotates about the axis of rotation 70, the rotating detectors define a generally circular imaging region, the precise shape of which may vary if the detectors are moved radially during rotation of the gantry 30. The detectors are mounted to the gantry 30 so as to be movable angularly with respect to the rotating gantry 30, radially toward and away from the axis of rotation 70, and tangentially with respect to the imaging region.

Figure 2:
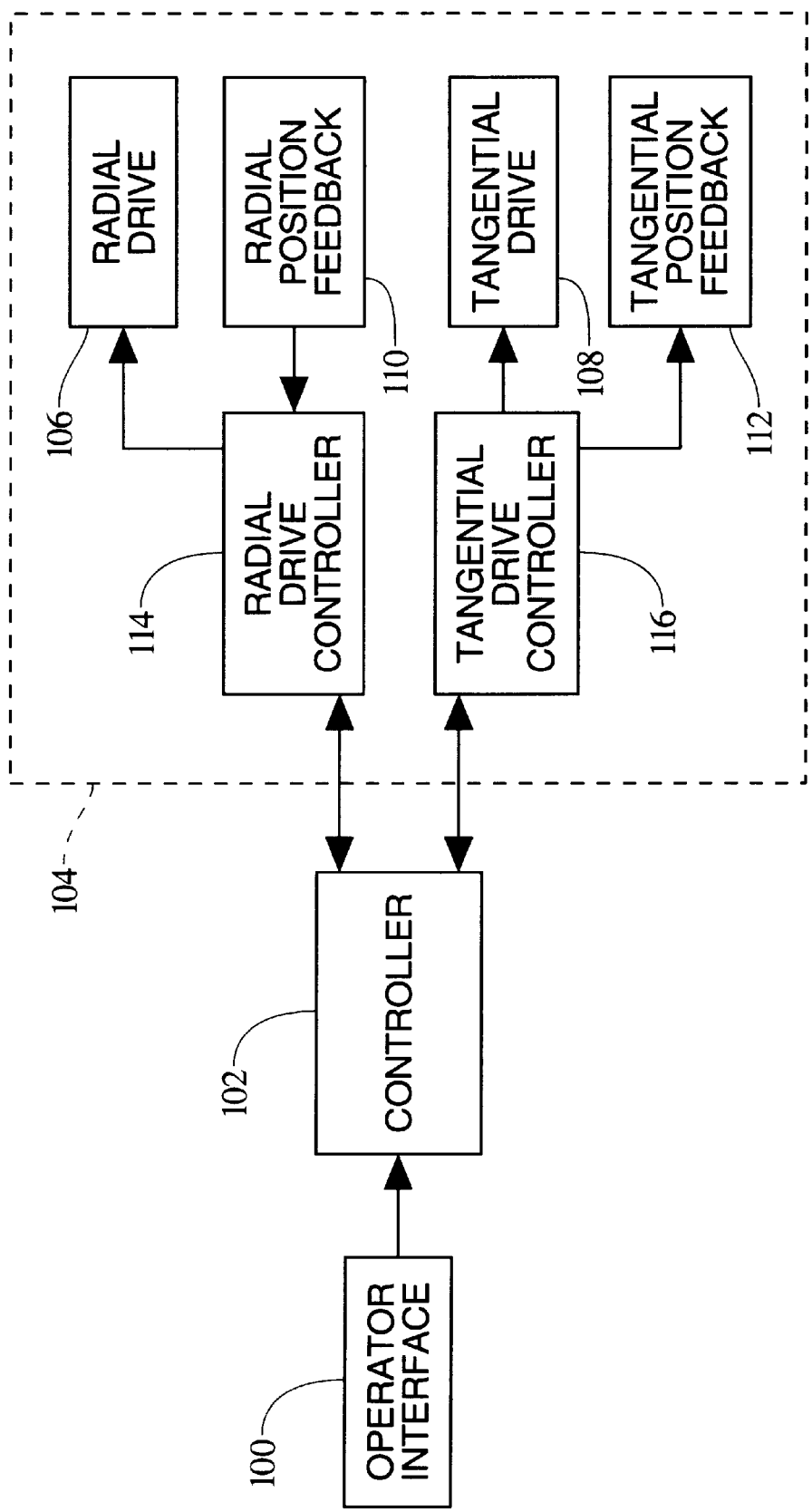
FIG. 2 depicts a system controller.
Figure 3A:
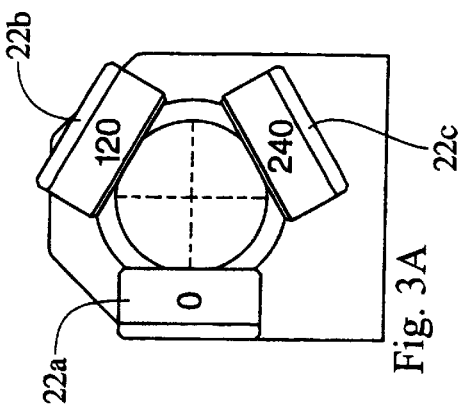
FIGS. 3a–3i depict various relative angular orientations of detector heads in a three detector head gamma camera.
Figure 3I:
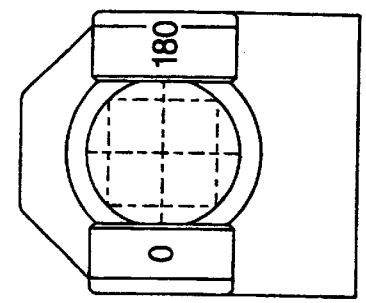
Figure 3D:
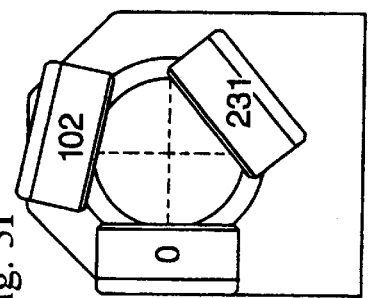
Figure 3F:
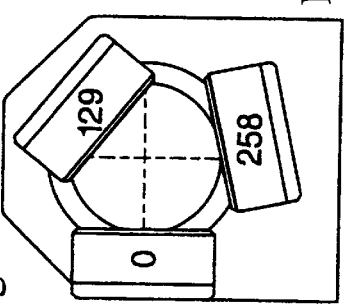
Figure 3H:
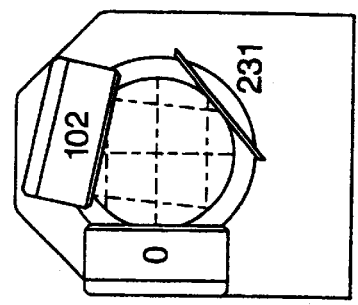
Figure 3C:
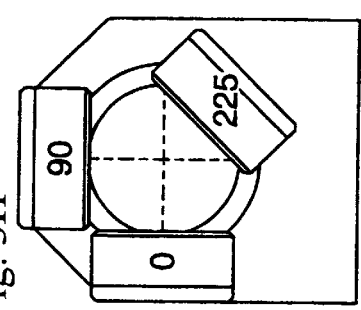
Figure 3E:
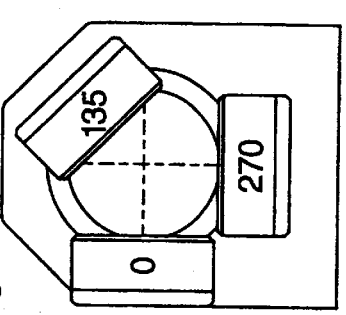
Figure 3G:
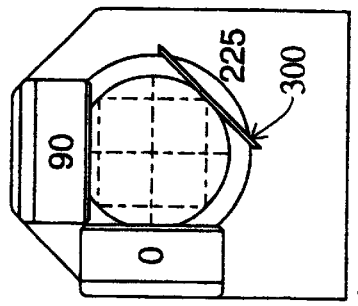
Figure 3B:
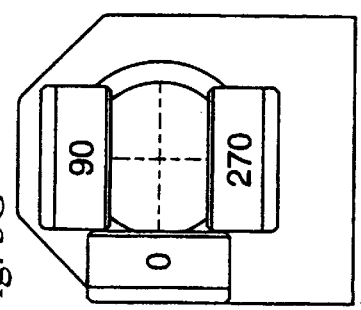

With reference to FIG. 2, the control mechanism for the detector head tangential and radial drive motions is described. Operator interface 100 includes an operator input device such as a keypad or keyboard and an operator output device such as a display or monitor. The operator may use the interface 100 to control and monitor the operation and scanning of the gamma camera. For example, the operator may in an automatic mode assume manual control of the detector head 22a, 22b, 22c positions. The operator may define a desired scan orbit configuration, and place the system in an automatic mode whereby the detector heads 22a, 22b, 22c are automatically moved to one or more desired positions.

The controller 102 calculates desired positions and velocities for the detector heads 22a, 22b, 22c based on the system mode and the commands entered by the operator. Associated with each detector head is a drive controller 104. Radial drives 106, 108 such as DC motors are used to vary the radial and tangential positions of the detector heads. Position feedback devices 110, 112 such as potentiometers and position encoders generate signals indicative of the detector head radial and tangential positions and velocities. Drive controllers 114, 116 command motion of the radial and tangential drives 106, 108 according to the desired positions determined by the controller 102. The controller also receives status, position, and velocity information for each of the drives. It will be appreciated that a drive controller 104 is provided for each detector head 22a, 22b, 22c. It will also be appreciated that the invention may also be used with drives other than DC motors, such as ac motors, stepper motors, or hydraulic actuators. Similarly, other feedback devices may be used.

Figure 4A:
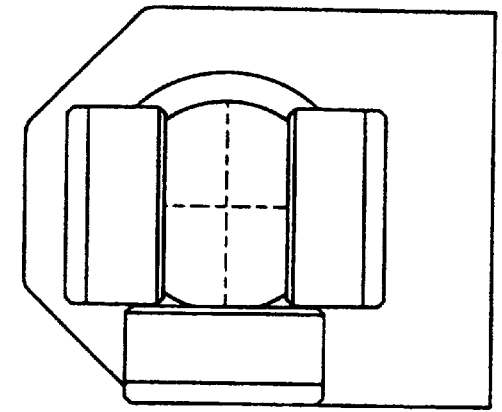
FIGS. 4a–4f depict various detector positions and motions in three and four head gamma cameras.
Figure 4B:
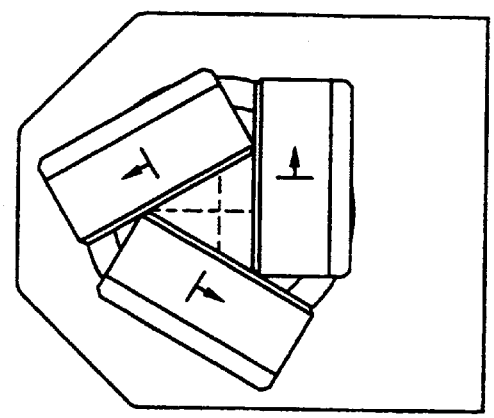

Examples of various relative detector angular relationships which may be advantageously implemented on a gamma camera system having three detector heads is shown in FIG. 3. As depicted by the radial arrows in FIG. 4a, the radial drives move the detectors 22a, 22b, 22c radially toward and away from the imaging region. As can be seen, the minimum aperture size and hence the minimum distance between the faces of the detectors and the patient is limited by the width of the detectors. They may be irised so that the minimum distance between the detector faces and the patient can be reduced from the limit otherwise defined by the detector widths. As depicted by the tangential arrows in FIG. 4b, the tangential drives permit the detectors to be moved in a direction generally tangential to the imaging region. As a result, mechanical interference between the corners of the detectors can be avoided, and the radial drives can be used to place the faces of the detectors closer to the patient. As shown in FIG. 4b, a portion of each detector face extends beyond the body of another detector. As will be appreciated, the width of each side of the aperture has a dimension smaller than the width of the corresponding detector.

The tangential and radial motions must be coordinated so that the detector heads 22a, 22b, 22c achieve their desired positions. One approach is to explicitly command all radial and tangential motion that may be needed to reach those positions. A drawback to this approach is that it is difficult to cover all possible gantry and detector configurations, thereby raising the possibility of a collision between the detectors or other undesirable motion.

Figure 5:
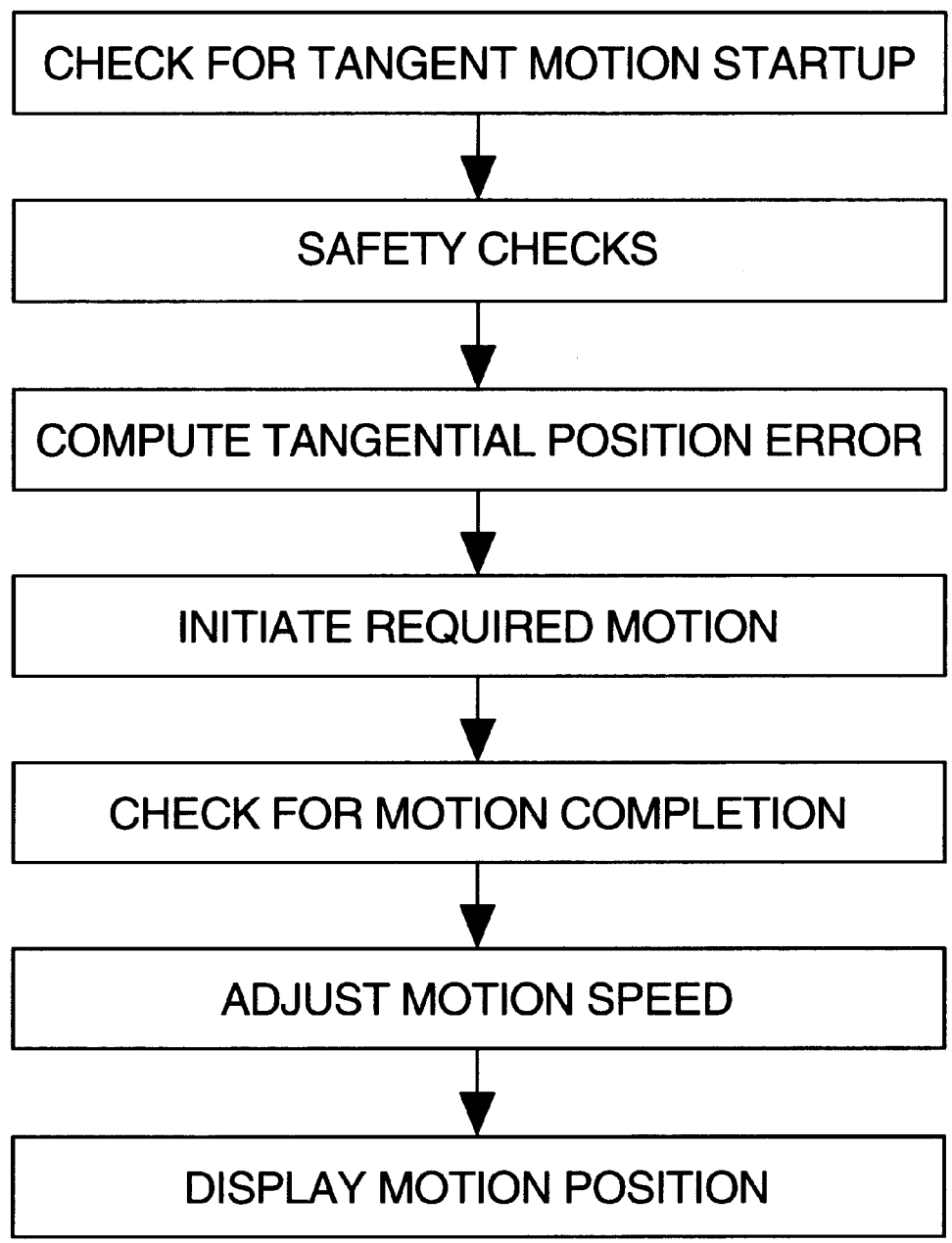
FIG. 5 depicts a motion monitor task.

Rather than attempting to predict all possible radial and tangential motion interactions, the desired tangential position may be computed periodically by the controller 102 based on detector radial positions and angulation. With reference to FIG. 5, the controller 102 periodically (e.g., every 10 ms) executes a motion monitor task. The controller 102 first checks for tangent motion startup and conducts various system safety checks to ensure that system motion is appropriate. The tangential position error is then computed, and any required motion (whether radial or tangential) is initiated. The controller checks for motion completion, sets the velocity of the required motion as needed, and displays the position of the detectors via the operator interface 100.

Figure 6:
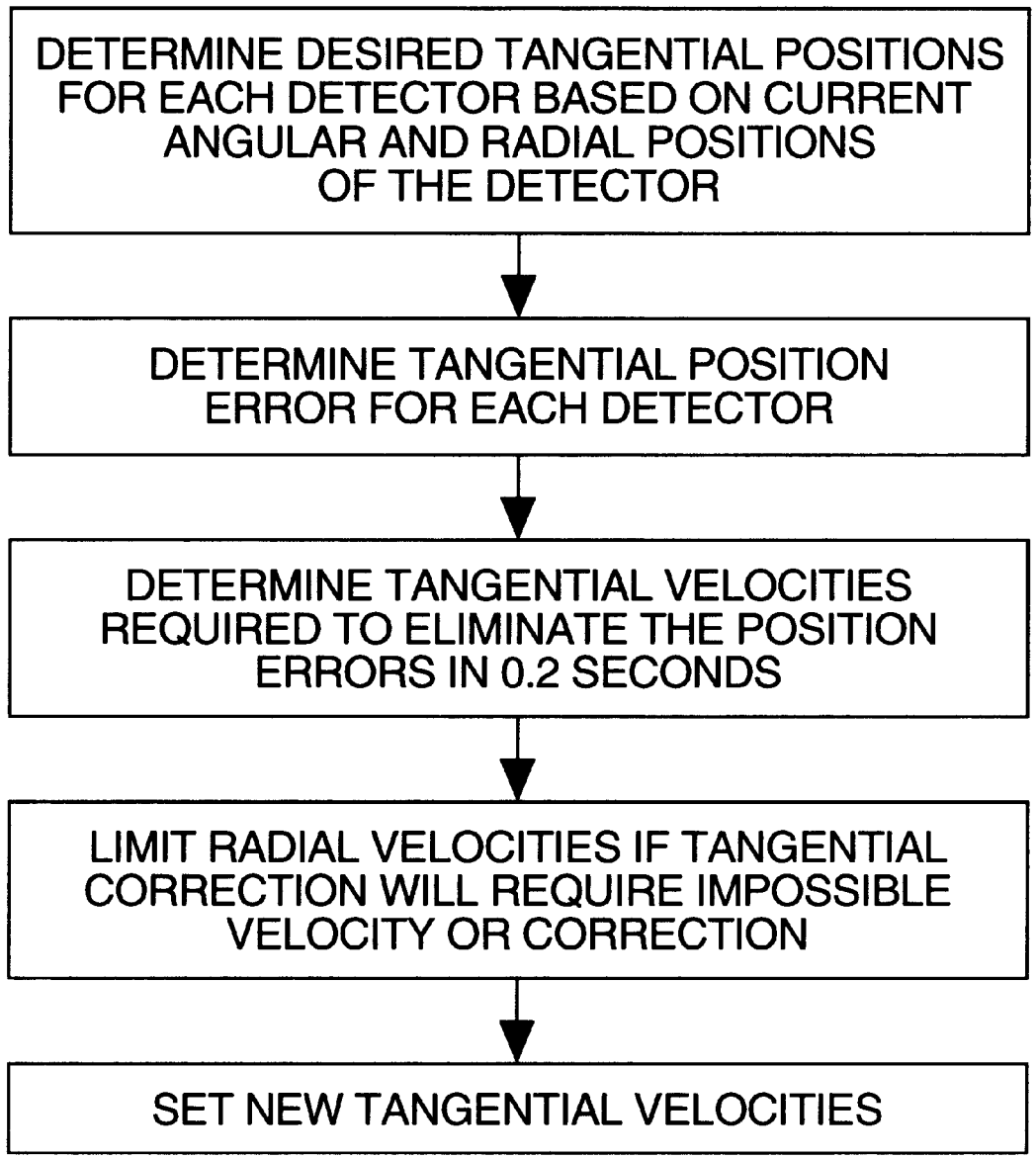
FIG. 6 depicts the determination of a tangential position error.

FIG. 6 depicts the determination of the tangential position error in greater detail. Based on the current angular and radial positions of each detector head, the desired tangential position of each detector head is determined. The difference between the desired and actual tangential position (e.g., the position error) for each detector head is determined, as is the tangential velocity required to eliminate the tangential position error within a desired time period. In a system where the maximum tangential and radial speeds are 1 cm/s, it has been determined that a time period of 200 ms yields satisfactory results. If the required tangential velocity is greater than the maximum speed of the tangential drive system, or if the tangential motion would result in an impossible condition (i.e., tangential motion beyond a position limit), the radial velocity is limited or the radial motion is stopped. Note that it is not necessary to limit the radial velocity when the detectors are being moved radially outward.

Figure 7:
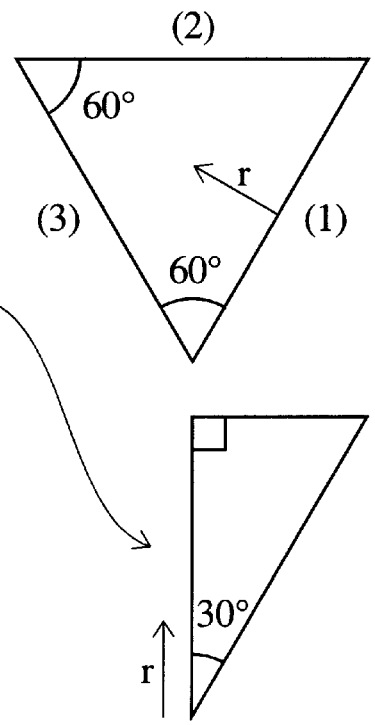
FIG. 7 depicts a tangential movement calculation.

An example of the geometry for a three detector, 120 degree approach is shown in FIG. 7. If, for example, it is desirable to move the radius −4.0 cm (in other words, make the radius smaller), it would be necessary to move each of the detectors tangentially by 6.92 cm. A particular benefit to causing equal tangential motion of all three detector heads is that the imaging center of rotation and the mechanical center of rotation remain the same.

Figure 4C:
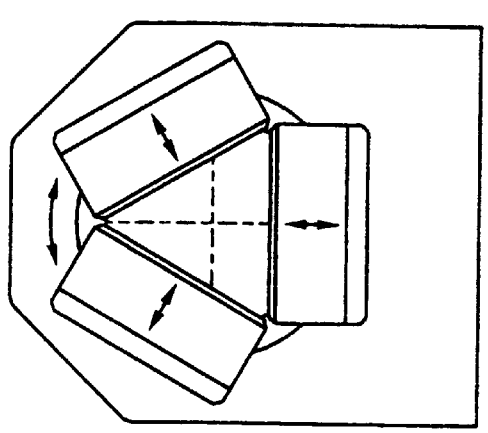
Figure 4E:
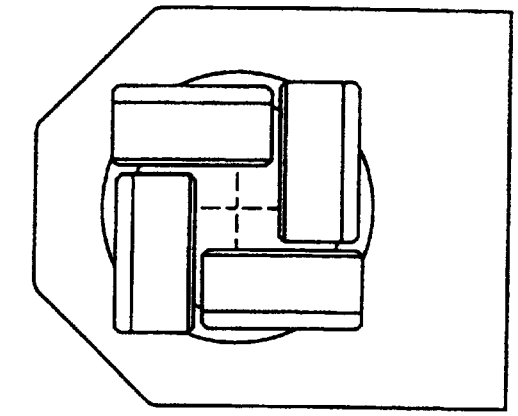
Figure 4D:
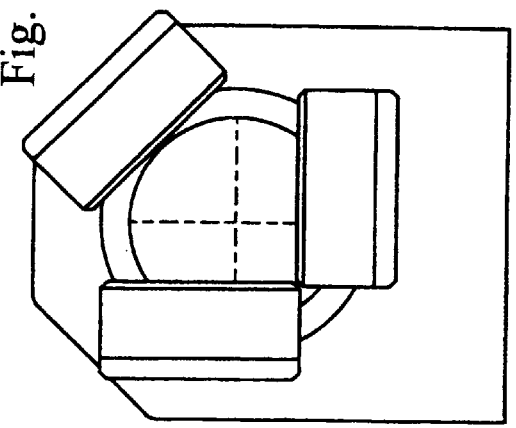
Figure 4F:
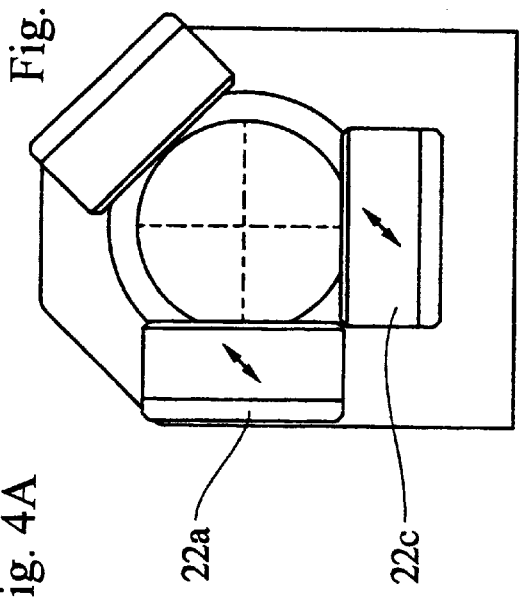
Figure 8:
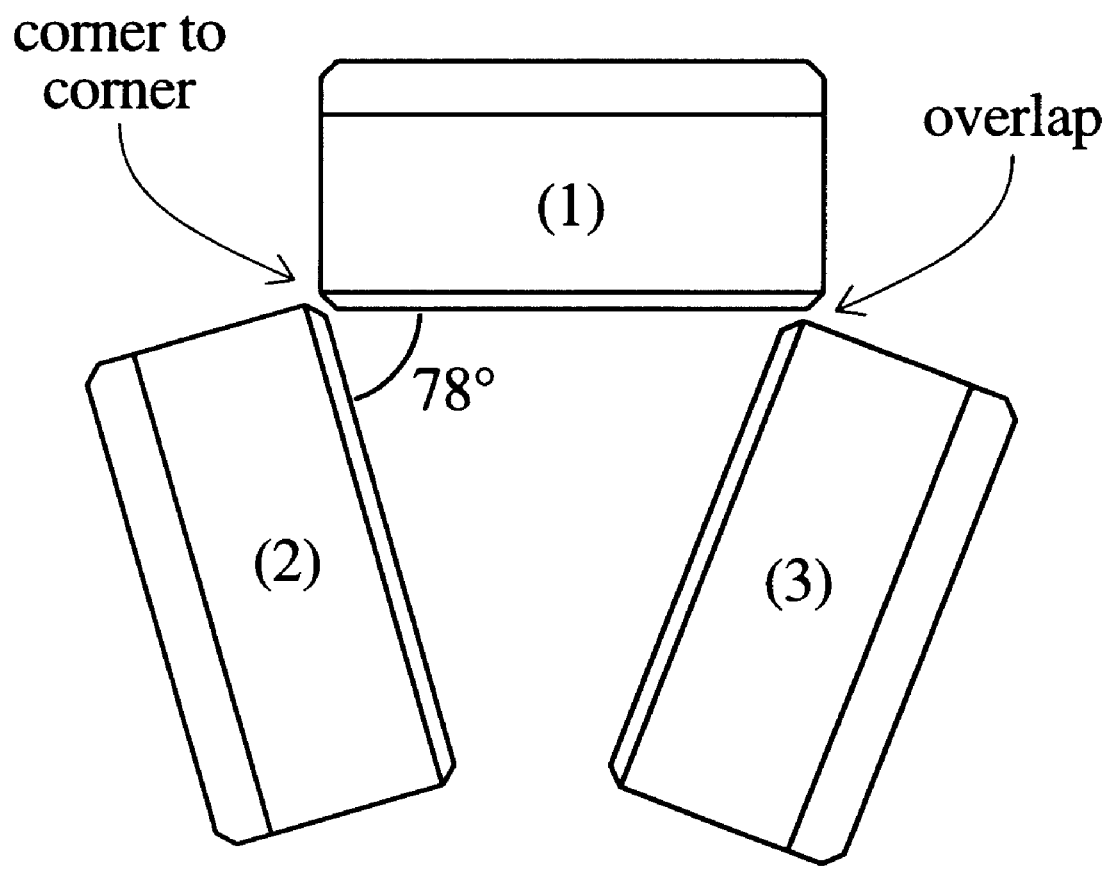
FIG. 8 depicts a detector configuration in a three detector head system.

In cases other than 120 degree detector configurations, the detectors are preferably operated such that the adjacent edges of the detectors align at their respective corners, for example as depicted in FIG. 4c. Another situation occurs in triple head configurations where the second and third heads are each at an angle of 78 degrees with respect to the first detector head as depicted in FIG. 8. In this case, the third detector overlaps the face of the first detector while the second detector maintains its corner relationship with the first detector. In any event, the tangential position error is calculated and the required tangential motion is initiated as described above.

Viewed from another perspective, the desired radial position of each of the detectors is treated as a master signal. Based on the current radial positions of the detectors, the difference between actual and desired tangential positions of each of the detectors is determined. These error signals are in turn used to drive the tangential motions in order to minimize the position errors. If the magnitude of the tangential position error cannot be reduced due to physical limitations in the tangential motion, the radial motion(s) which contribute to the error are commanded to reduce speed or stop to prevent further increases in the tangential position errors.

The invention has been described with reference to the preferred embodiment. Obviously, modifications and alterations will occur to others upon reading an understanding the preceding description. It is intended that the invention be construed as including all such modifications and alterations insofar as they come within the scope of the appended claims or the equivalents thereof.

I claim:

1. A method of imaging utilizing a gamma camera having first and second detectors disposed about an examination region, the method comprising:

placing the detectors in a desired position with respect to the examination region, the step of placing including determining an actual position of the first detector; and moving the second detector based on the actual position of the first detector;

utilizing the detectors to detect radiation; and generating an image indicative of the detected radiation.

2. The method of claim 1 wherein the first detector is movable in a radial direction with respect to the examination region and the second detector is movable in a tangential direction with respect to the examination region, the step of placing including determining an actual radial position of the first detector;

moving the second detector in a tangential direction based on the actual radial position of the first detector.

3. The method of claim 1 wherein the step of placing includes determining a desired motion for the second detector based on the actual position of the first detector;

comparing the desired motion to a limit;

limiting a motion of the first detector if the desired motion exceeds the limit.

4. The method of claim 3 including determining a desired tangential motion for the second detector based on the actual radial position of the first detector.

5. The method of claim 4 wherein the gamma camera includes a third detector and including determining a desired tangential motion for the second detector based on the actual radial positions of the first and third detectors.

6. The method of claim 3 wherein the step of determining a desired motion includes determining a desired velocity, the limit includes a limit velocity, and the step of comparing includes comparing the desired velocity to the limit velocity.

7. The method of claim 6 wherein the step of determining a velocity includes determining a difference between the actual position of the second detector and the desired position of the second detector and determining a velocity required for the second detector to reach the actual position within a first time period.

8. The method of claim 3 wherein the step of determining a desired motion includes determining a desired position, the limit includes a limit position, and the step of comparing includes comparing the desired position to the limit position.

9. The method of claim 3 wherein limiting a motion includes limiting a velocity of the first detector.

10. The method of claim 1 wherein the gamma camera includes a third detector and the step of placing includes determining an actual position of the first, second, and third detectors, moving the first detector based on the actual position of the second and third detectors, moving the second detector based on the actual position of the first and third detectors, and moving the third detector based on the actual position of the first and second detectors.

11. The method of claim 10 wherein the first, second, and third detectors are each movable radially with respect to the examination region and tangentially with respect to the examination region and the step of placing includes determining an actual radial position of the first, second, and third detectors, moving the first detector in a tangential direction based on the actual radial positions of the second and third detectors, moving the second detector in a tangential direction based on the actual radial position of the first and third detectors, and moving the third detector in a tangential direction based on the actual radial positions of the first and second detectors.

12. The method of claim 11 wherein the detectors are disposed at equal angular intervals about the examination region.

13. A method of imaging utilizing a gamma camera having first and second detectors disposed about an examination region, the method comprising:

placing the detectors in a desired position with respect to the examination region, the step of placing including determining a position of the first detector;
        determining a desired motion for the second detector based on the position of the first detector;
        comparing the desired motion to a limit; and
        limiting a motion of the first detector if the desired motion exceeds the limit;
    utilizing the detectors to detect radiation; and
    generating an image indicative of the detected radiation.

14. The method of claim 13 wherein the desired motion includes a velocity and the limit is a maximum velocity, the step of placing including limiting a motion of the first detector if the desired velocity of the second detector is greater than the maximum velocity.

15. The method of claim 13 wherein the step of placing includes determining a radial position of the first detector, determining a desired tangential motion for the second detector based on the radial position of the first detector, and limiting a radial motion of the first detector if the desired tangential motion exceeds the limit.

16. In a gamma camera having first, second, and third detectors disposed about an examination region, a method of positioning the detectors with respect to the examination region comprising the steps of:

determining a radial position of the second and third detectors;
    utilizing the radial positions of the second and third detectors to determine a desired tangential velocity for the first detector;
    comparing the desired tangential velocity to a limit velocity;
    if the desired tangential velocity is greater than the limit velocity, limiting a radial velocity of at least one of the second and third detectors.

\* \* \* \* \*